(12) United States Patent
Huang et al.

(10) Patent No.: US 8,524,166 B2
(45) Date of Patent: ***Sep. 3, 2013

(54) STENT AND DELIVERY SYSTEM WITH REDUCED CHEMICAL DEGRADATION INCLUDING A CHITOOLIGOSACCHARIDE

(75) Inventors: Bin Huang, Pleasanton, CA (US);
Lothar W. Kleiner, Los Altos, CA (US);
John Stankus, Campbell, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/418,244

(22) Filed: Mar. 12, 2012

(65) Prior Publication Data

US 2012/0171260 A1 Jul. 5, 2012

Related U.S. Application Data

(63) Continuation of application No. 11/804,234, filed on May 16, 2007, now Pat. No. 8,147,769.

(51) Int. Cl.
*A61K 39/02* (2006.01)
*A61L 2/00* (2006.01)

(52) U.S. Cl.
USPC ............................................ 422/243; 422/22

(58) Field of Classification Search
USPC .................................................. 422/22, 243
See application file for complete search history.

(56) References Cited

U.S. PATENT DOCUMENTS

| | | | |
|---|---|---|---|
| 3,993,622 | A | 11/1976 | Brunetti |
| 4,401,804 | A | 8/1983 | Wooten et al. |
| 4,801,749 | A | 1/1989 | Kazmierczak et al. |
| 4,803,259 | A | 2/1989 | Zboril et al. |
| 4,880,856 | A | 11/1989 | Avakian |
| 5,155,145 | A | 10/1992 | Foster et al. |
| 5,284,886 | A | 2/1994 | Reilly et al. |
| 5,484,881 | A | 1/1996 | Gruber et al. |
| 5,496,923 | A | 3/1996 | Suizu et al. |
| 5,574,082 | A | 11/1996 | Keller et al. |
| 5,648,412 | A | 7/1997 | Mistry et al. |
| 5,686,540 | A | 11/1997 | Kakizawa |
| 5,968,429 | A | 10/1999 | Treece et al. |
| 5,981,510 | A | 11/1999 | Fujiwara et al. |
| 6,143,863 | A | 11/2000 | Gruber et al. |
| 6,506,411 | B2 | 1/2003 | Hunter et al. |
| 6,673,385 | B1 | 1/2004 | Ding et al. |
| 6,759,431 | B2 | 7/2004 | Hunter et al. |
| 6,949,254 | B2 | 9/2005 | Gen |

(Continued)

FOREIGN PATENT DOCUMENTS

| | | |
|---|---|---|
| WO | WO 98/41559 | 9/1998 |
| WO | WO 02/34311 | 5/2002 |

(Continued)

OTHER PUBLICATIONS

"Final Report on the Amended Safety Assessment of Propyl Gallate", International J. of Toxicology, 26, Suppl. 3, pp. 89-118 (2007).

(Continued)

*Primary Examiner* — Kevin Joyner
(74) *Attorney, Agent, or Firm* — Squire Sanders (US) LLP

(57) ABSTRACT

Stents and delivery systems with reduced chemical degradation and methods of sterilizing the same are disclosed.

8 Claims, 3 Drawing Sheets

(56) References Cited

U.S. PATENT DOCUMENTS

| | | |
|---|---|---|
| 7,268,205 B2 | 9/2007 | Williams et al. |
| 7,332,535 B2 | 2/2008 | Kröhnke et al. |
| 7,794,495 B2 | 9/2010 | Gale et al. |
| 7,998,404 B2 | 8/2011 | Huang et al. |
| 8,147,769 B1 | 4/2012 | Huang et al. |
| 2002/0051730 A1 | 5/2002 | Bodnar et al. |
| 2003/0228475 A1 | 12/2003 | Komada |
| 2004/0249450 A1 | 12/2004 | Ishii |
| 2005/0070997 A1 | 3/2005 | Thornton et al. |
| 2005/0106210 A1 | 5/2005 | Ding et al. |
| 2005/0148720 A1 | 7/2005 | Li et al. |
| 2005/0244459 A1 | 11/2005 | DeWitt et al. |
| 2005/0267560 A1 | 12/2005 | Bates |
| 2006/0013849 A1 | 1/2006 | Strickler et al. |
| 2006/0246149 A1 | 11/2006 | Buchholz et al. |
| 2007/0104801 A1 | 5/2007 | Cecchi et al. |
| 2007/0128343 A1 | 6/2007 | Chappa |
| 2007/0208420 A1 | 9/2007 | Ameer et al. |
| 2007/0231363 A1 | 10/2007 | Chen et al. |
| 2007/0232169 A1 | 10/2007 | Strickler et al. |
| 2007/0281073 A1 | 12/2007 | Gale et al. |
| 2008/0020045 A1 | 1/2008 | Chappa et al. |
| 2008/0038354 A1 | 2/2008 | Slager et al. |
| 2010/0209472 A1 | 8/2010 | Wang |

FOREIGN PATENT DOCUMENTS

| | | |
|---|---|---|
| WO | WO 2004/000383 | 12/2003 |
| WO | WO 2006/138406 | 12/2006 |
| WO | WO 2007/133400 | 11/2007 |

OTHER PUBLICATIONS

"Processing & Thermal Stability—Generic Effect", Value beyond chemistry, 2 pgs. (2000).

Antioxidants, Anionic Polymerization vol. 5, Encyclopedia of Polymer Science and Technology, pp. 164-197, no date.

Antioxidants, Product Lines Reviewed, Plastics Technology, from Free Online Library, 5 pgs. 2008.

Babanalbandi et al., "Thermal stability of poly(lactic acid) before and after γ-radiolysis", Polym. Int. 48, pp. 980-984 (1999).

Bauer et al., "Antioxidant interaction between organic phosphites and hindered amine light stabilizers during processing and thermoxidation of polypropylene", Polymer degradation and stability, vol. 48, No. 3, 1 pg. Abstract only (1995).

Chan, *Vitamin E and Atherosclerosis*, JN the Journal of Nutrition, pp. 1593-1596, jn.nutrition.org (2007).

Chemical Database, "1,2-Bis(3,5-Di-Tert-Butyl-4-Hydroxyhydrocinnamoyl) Hydrazide", EnvironmentalChemistry.com, 1 pg. (2008).

Colin et al., "Polymer degradation during processing", Comptes Rendus Chimie, vol. 9, issues 11-12, 1 pg. Abstract only (2006).

Cryptand, Sci-Tech Dictionary, downloaded from www.answers.com/topic/cryptand, Apr. 4, 2008, 3 pgs.

Gupta et al., "Thermal oxidative degradation of poly-lactic acid", Colloid & Polymer Science vol. 260, pp. 308-311 (1982).

Hall III et al., "Comparison Between Capillary Electrophoresis and High-Performance Liquid Chromatography Separation of Food Grade Antioxidants", J. Agric. Food Chem. 42, pp. 919-921 (1994).

Kopinke et al., "Thermal decomposition of biodegradable polyesters-II. Poly(lactic acid)", Polymer Degradation and Stability 53, pp. 329-342 (1996).

Kricheldorf et al., "Poly(lactones). Polymerization Mechanism of Metal Alkoxide Initiated Polymerizations of Lactide and Various Lactones", Macromolecules vol. 21, pp. 286-293 (1988).

Mayzo "BNX® MD-1024 Antioxidant & Metal Deactivator", product data sheet, 3 pgs. (2005).

McNeill et al., "Degradation Studies of Some Polyesters and Polycarbonates-1. Polylactide: General Features of the Degradation Under Programmed Heating Conditions", Polymer Degradation and Stability vol. 11, pp. 267-285 (1985).

McNeill et al., "Degradation Studies of Some Polyesters and Polycarbonates-2. Polylactide: Degradation Under Isothermal Conditions, Thermal Degradation Mechanism and Photolysis of the Polymer", Polymer Degradation and Stability vol. 11, pp. 309-326 (1985).

Mohamed, "N-Acryloyl, N'-cyanoacetohydrazide as a thermal stabilizer for rigid poly(vinyl chloride)", Polymer Int. vol. 45, No. 2, 1 pg. Abstract only (1998).

Sandeep Nema et al., "Excipients: Parenteral Dosage Forms and Their Role", Encyclopedia of Pharm. Technology, pp. 1622-1644 (2007).

Soo-Hong Lee et al., "Synthesis and Degradation of End-Group—Functionalized Polylactide", J. of Polymer Science: Part A: Polymer Chem. vol. 39, pp. 973-985 (2001).

Soulti et al., "Inhibition of butter oxidation by some phenolics", Eur. J. Lipid Sci. Tech. 109, pp. 706-709 (2007).

Valenzuela et al., "Inhibitory action of conventional food-grade natural antioxidants and of natural antioxidants of new development on the thermal-induced oxidation of cholesterol", Int. J. of Food Sciences and Nutrition, vol. 55, No. 2, pp. 155-162 (2004).

STENT AND DELIVERY SYSTEM WITH REDUCED CHEMICAL DEGRADATION INCLUDING A CHITOOLIGOSACCHARIDE

CROSS-REFERENCE TO RELATED APPLICATIONS

This application is a continuation of U.S. application Ser. No. 11/804,234, filed on May 16, 2007, and issuing as U.S. Pat. No. 8,147,769 B1 on Apr. 3, 2012, which is incorporated by reference as if fully set forth, including any figures, herein.

BACKGROUND OF THE INVENTION

1. Field of the Invention

This invention relates to a reducing chemical degradation to medical articles due to sterilization.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

A stent and delivery system typically undergo sterilization to reduce their bioburden to an acceptable sterility assurance level (SAL). There are numerous methods of sterilizing medical devices, the most common being ethylene oxide treatment and treatment with ionization radiation such as electron beam and gamma radiation. Generally, it is desirable for the sterilization procedure to have little or no adverse affects on the performance of a sterilized article.

SUMMARY

Various embodiments of the present invention include a stent comprising: a substrate; a coating comprising a polymer over the substrate; and a chemical degradation-reducing substance that reduces or prevent chemical degradation in a polymeric portion of the stent, the chemical degradation arising from exposure to radiation during sterilization.

Additional embodiments of the present invention include a stent delivery assembly comprising a polymeric portion of the assembly, the polymeric portion including a chemical degradation-reducing substance that reduces or prevents chemical degradation in the polymeric portion arising from exposure to radiation during sterilization.

Further embodiments of the present invention include a method of sterilizing a stent delivery assembly, the method comprising exposing a stent delivery assembly to radiation to reduce the bioburden of the assembly, wherein a polymeric portion of the assembly includes a substance that reduces or prevents chemical degradation in the polymeric portion arising from the exposure to the e-beam radiation.

DETAILED DESCRIPTION OF THE INVENTION

Various embodiments of the present invention relate to reducing or preventing chemical degradation to polymeric-containing portions of stents and stent delivery assemblies due to radiation sterilization. Embodiments also include reducing or preventing chemical degradation to drugs or active agents on stents.

The embodiments described herein may be may be applied generally to implantable medical devices and delivery systems for implantable medical devices. The embodiments are particularly relevant, for reasons discussed below, to implantable medical devices, such as a stents, having a polymeric substrate, a polymer-based coating, a drug-delivery coating, or a combination thereof. A polymer-based coating may contain, for example, an active agent or drug for local administration at a diseased site. An implantable medical device may include a polymer or non-polymer substrate such as metal with a polymer-based coating.

Examples of implantable medical devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Abbott Cardiovascular Systems Inc., Santa Clara, Calif.). The underlying structure or substrate of the device can be of virtually any design.

The embodiments herein are also generally applicable to a delivery systems or assemblies used to implant an implantable medical device. The embodiments are particularly relevant, to stent delivery systems for delivering stents at a treatment site. Various sections of stent delivery systems, such as the catheter, stent delivery balloon, and restraining sheath, can be composed in whole or in part of polymers. Such sections can also be composed of composite metal polymer material. Representative materials that can be used to form sections of a stent delivery assembly include, but are not limited to, polyetheretherketones (PEEK), polypropylene, low density polyethylene, high density polyethylene, ethylene vinyl acetate, nylon, polyesters, polyethylene terephthalate, Surlyn™, Pebax®, and polyurethanes.

Figure 1:
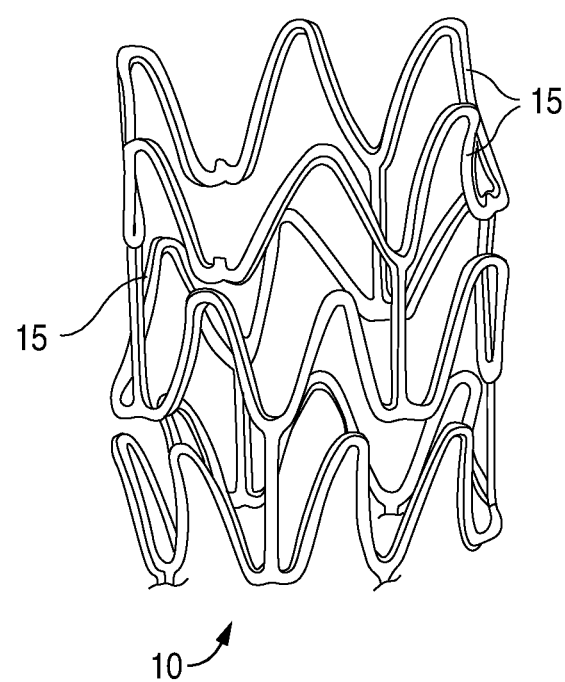
FIG. 1 depicts a stent.

FIG. 1 depicts a view of a stent 10. In some embodiments, a stent may include a pattern or network of interconnecting structural elements 15. Stent 10 may be formed from a tube (not shown). The pattern of structural elements 15 can take on a variety of patterns. The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited. A stent such as stent 10 may be fabricated from a tube by forming a pattern with a technique such as laser cutting or chemical etching.

A stent such as stent 10 may be fabricated from a polymeric tube or a sheet by rolling and bonding the sheet to form a tube. A stent pattern may be formed on a polymeric tube by laser cutting a pattern on the tube. Representative examples of lasers that may be used include, but are not limited to, excimer, carbon dioxide, and YAG. In other embodiments, chemical etching may be used to form a pattern on a tube.

Figure 2:
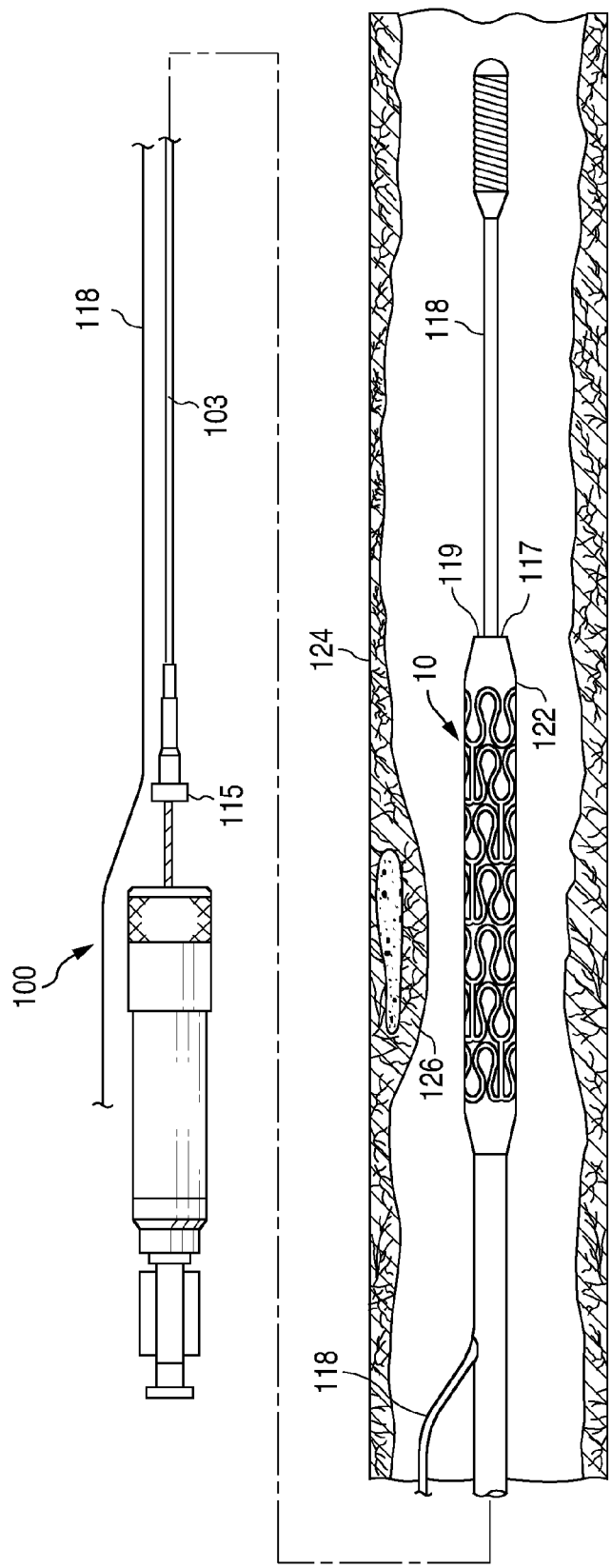
FIG. 2 depicts a stent mounted on a stent delivery assembly.

FIG. 2 depicts stent 10 mounted on a stent delivery assembly 100 which is used to deliver the stent and implant it in an artery 124, peripheral artery, or other vessel or lumen within the body. Stent delivery assembly 100 shown in FIG. 2 includes a catheter 103 which has a proximal end 115 and a distal end 117. The stent delivery assembly is configured to advance through the patient's vascular system by advancing over a guide wire by any of the well known methods.

Stent delivery assembly 100 as depicted in FIG. 2 includes a port 120 where a guide wire 118 will exit the catheter. The distal end of the guide wire exits catheter distal end 119 so that the catheter advances along the guide wire on a section of the catheter between the port 120 and the catheter distal end. Stent 10 is mounted on an expandable member 122 (balloon) and is crimped tightly thereon so that stent 100 and expandable member 122 present a low profile diameter for delivery through the coronary arteries.

In a typical procedure to implant stent 100, guide wire 118 is advanced through the patient's vascular system by well known methods so that the distal end of the guide wire is advanced past a diseased area 126. Thereafter, stent delivery assembly 100 is advanced over the guide wire so that the stent assembly is positioned in the target area. Expandable member or balloon 122 is inflated by well known means so that it expands radially outwardly and in turn expands the stent radially outwardly until the stent is apposed to the vessel wall. The expandable member is then deflated and the catheter withdrawn from the patient's vascular system.

Sterilization is typically performed on medical devices, such as stents and delivery systems, to reduce the bioburden. Bioburden refers generally to the number of microorganisms with which an object is contaminated. The degree of sterilization is typically measured by a sterility assurance level (SAL) which refers to the probability of a viable microorganism being present on a product unit after sterilization. The required SAL for a product is dependent on the intended use of the product. For example, a product to be used in the body's fluid path is considered a Class III device. SAL's for various medical devices can be found in materials from the Association for the Advancement of Medical Instrumentation (AAMI) in Arlington, Va.

Radiation sterilization is well known to those of ordinary skill the art. Medical articles composed in whole or in part of polymers can be sterilized by various types of radiation, including, but not limited to, electron beam (e-beam), gamma ray, ultraviolet, infra-red, ion beam, x-ray, and laser sterilization. A sterilization dose can be determined by selecting a dose that provides a required SAL. A sample can be exposed to the required dose in one or multiple passes.

However, it is known that radiation can degrade the properties of the polymers and drugs being exposed to the radiation. In particular, the radiation can induce chemical radiation of the polymer and drug. High-energy radiation such as e-beam and gamma radiation tends to produce ionization and excitation in polymer molecules. These energy-rich species undergo dissociation, subtraction, and addition reactions in a sequence leading to chemical stability. The stabilization process can occur during, immediately after, or even days, weeks, or months after irradiation which often results in physical and chemical cross-linking or chain scission. Chain scission can result in a reduction in molecular weight. Resultant physical changes can include embrittlement, discoloration, odor generation, stiffening, and softening, among others.

In particular, the deterioration of the performance of polymeric materials and drugs due to e-beam radiation sterilization has been associated with free radical formation in polymer-containing portions of devices exposed to e-beam radiation. "Free radicals" refer to atomic or molecular species with unpaired electrons on an otherwise open shell configuration. Free radicals can be formed by oxidation reactions.

These unpaired electrons are usually highly reactive, so radicals are likely to take part in chemical reactions, including chain reactions. The free radicals formed due to radiation exposure can react with the polymer chains of the polymer-containing portions resulting in degradation of the polymer. The reactions are dependent on e-beam dose and temperature.

Furthermore, the release rate of a drug in a polymer-containing portion of device can be adversely affected by the degradation of the polymer. In addition, drugs in the polymer-containing portions are also subject to chemical degradation due to free radical formation induced by radiation exposure. Drugs can also chemically degrade due to increased temperatures induced by the e-beam radiation.

Stents and delivery systems are typically sterilized, packaged, stored, and transported in a "ready to implant" configuration in which the stent is disposed at the distal end of a catheter of a delivery system. A sheath can also be disposed over the stent to secure the stent to the balloon. Stents and stent delivery assemblies can additionally be stored, transported, as well as sterilized in flexible, sealed storage containers, such as a foil pouch, that protects the stent and assembly from damage and environmental exposure (humidity, oxygen, light, etc.) which can have an adverse effect on the stent and delivery system. Such containers can be in the form of a pouch or sleeve. For example, the container can be constructed of two sheets or lamina which have been joined along an edge. Also, the container can be constructed of a single sheet or lamina which has been folded and sealed along all edges or along all non-folded edges; or a bag or pocket which is sealed along one or more edges. The pouches can be made from a polymer, glass, ceramic, metallic substance, or a combination thereof. A pouch containing a stent and delivery system can be further disposed within a rigid container to protect the pouch and the stent and delivery system contained therein. The rigid container can be, for example, a box, such as a chipboard box.

Figure 3:
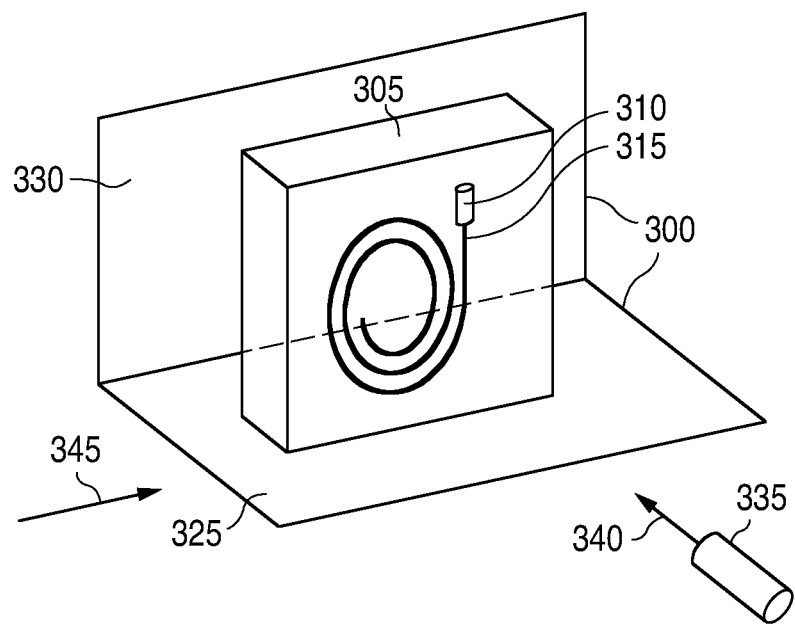
FIG. 3 depicts a schematic illustration of a fixture that supports a package containing a stent disposed on a stent-delivery assembly.

A system for sterilizing a packaged stent delivery assembly includes a radiation source, such as an e-beam source, and a fixture for supporting the package. The support fixture is moved, for example, on a conveyer arrangement past an e-beam source in a manner that an e-beam is directed onto the stent delivery system assembly. FIG. 3 depicts a schematic illustration of a fixture 300 that supports a package 305 containing a stent 310 disposed on a stent-delivery assembly 315. Fixture 300 includes a bottom support 325 and a back support arm 330. A radiation source 335 directs radiation as shown by an arrow 340. Fixture 300 can be moved by a conveyer system (not shown) as shown by an arrow 345 past radiation source 335 to sterilize the stent-delivery system assembly in container 305.

Various embodiments of the present invention include stents and stent delivery assemblies that have a substance in or on polymer-containing portions that reduce or prevent chemical degradation induced by radiation used to sterilize the stents and stent delivery assemblies. Such substances can also reduce or prevent chemical degradation of drugs within polymer-containing portions of stents. In such embodiments, the substance can be incorporated within or on a polymer-containing portion such as a stent or stent delivery assembly.

As noted above, e-beam radiation exposure to a polymer can lead to free radical formation within the polymer. In certain embodiments, the substance for reducing or preventing chemical degradation can be a free radical scavenger or antioxidant. "Free radical scavengers" or "antioxidants" are molecules that slow or prevent the oxidation of other chemicals. Free radical scavengers or antioxidants can remove free radical intermediates that can participate in chain reactions, thus terminating such reactions. Free radical scavengers or antioxidants can also inhibit other oxidation reactions by being oxidized themselves. In certain embodiments of the present invention, free radical scavengers or antioxidants remove free radicals that can cause chain reactions that result in chemical degradation of a polymer-containing portion of a stent or stent delivery assembly.

As shown in FIG. 1, a stent can include a substrate or scaffolding that is designed to support the walls of a body lumen. In some embodiments, the stent substrate can be formed from a polymer, such as a bioabsorbable polymer. A substance such as a free radical scavenger or antioxidant that reduces or prevents chemical degradation due to radiation exposure can be mixed or dispersed within the polymer. The substance can reduce or prevent chemical degradation to a degree that causes degradation of mechanical properties of the substrate. Such mechanical properties can be strength, toughness, and stiffness. A stent substrate can include 0.001-5 wt %, 0.01-2 wt %, or more narrowly, 0.01-1 wt % of a free radical scavenger or antioxidant.

As noted above, a polymer stent substrate can be fabricated from a polymer tube. Polymer constructs such as tubes can be formed by extrusion. Prior to extrusion, the chemical degradation-reducing substance can be incorporated into a polymer through solution blending, melt blending, or a combination thereof. In some embodiments, the substance may be part of the polymer molecule, i.e., covalently bonded to the polymer rather than mixed.

The polymer with the substance can then be extruded to form a tube. Alternatively or additionally, the substance can be mixed or compounded with the polymer during extrusion. A laser can then be used to cut a pattern in the tube.

Figure 4:
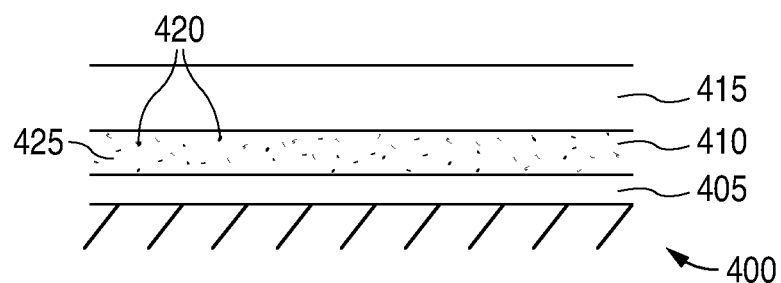
FIG. 4 depicts a close-up schematic view of a stent surface showing a stent substrate with a coating.

In further embodiments, a stent with either a metal or polymer substrate can include a polymer-containing coating that includes a chemical degradation-reducing substance such as a free radical scavenger or antioxidant. A stent coating can include various types of coating layers including, but not limited to, a drug-polymer layer, a primer layer, and a topcoat layer. FIG. 4 depicts a close-up schematic view of a stent surface showing a stent substrate 400. Substrate 400 includes a coating with a primer layer 405, a drug-polymer layer 410, and a topcoat layer 415. Drug-polymer layer 405 includes an active agent or drug 420 dispersed within a polymer carrier 425.

A primer layer is typically disposed between a stent substrate and a drug-polymer layer to facilitate adhesion between the substrate and the drug-polymer layer. The topcoat layer is a polymer typically disposed above a drug-polymer layer to control the rate of delivery of the drug into the body from the drug-polymer layer. A coating layer can include 0.001-10 wt %, 0.01-5 wt %, 0.01-2 wt %, or more narrowly, 0.01-1 wt % of a free radical scavenger or antioxidant.

Various embodiments can include incorporating the chemical degradation-reducing substance in one or more of the layers of the coating. The various layers and the substrate can have the same substance and the same concentration by weight or volume in each layer. Alternatively, the layers may have different concentrations of the substance, depending on the desired or required protection from chemical degradation caused by radiation. For example, a drug-polymer layer may have a higher concentration of the substance than other layers or than the stent substrate. Additionally, in some embodiments, at least one layer may have a different type of free radical scavenger or antioxidant than other layers. The type of free radical scavenger or antioxidant can be selected based on desired protection from chemical degradation.

The type and amount of free radical scavenger selected for a layer can be selected based on a desired or necessary protection from chemical degradation. For instance, it is important for each of the layers to have sufficient toughness and flexibility to resist cracking and delamination. In particular, a primer layer can include sufficient amount of the substance to reduce or prevent chemical degradation that could reduce the adhesion of the primer layer to the substrate. In addition, the drug-polymer layer can include a substance to reduce or prevent chemical degradation of the polymer carrier for the drug and the drug within the polymer carrier. The drug-polymer layer can include a sufficient amount of the substance to reduce or prevent radiation from degrading the drug and modifying the mechanical properties and the drug elution properties of the carrier polymer. Additionally, the topcoat layer can include a sufficient amount of the substance to prevent radiation from significantly modifying the mechanical properties and the drug elution properties of the topcoat layer polymer.

Additionally, the type of free radical scavenger or antioxidant can be selected based on the type of polymer of the stent substrate or coating layer. Only specific types of free radical scavengers or antioxidants may be capable of reducing or preventing chemical degradation in a specific polymer.

The incorporated free radical scavengers and antioxidants may be released through diffusion or material degradation during delivery and after implantation. Additionally, a free radical scavenger or antioxidant can be selected based on its therapeutic affect upon implantation. In addition to reducing chemical degradation, the presence of free radical scavengers or antioxidants in a polymer stent substrate or within a polymer coating can have a therapeutic benefit when they are released into the body. For example, it has been demonstrated that Vitamin E can protect against atherosclerosis in both animals and humans. A. C. Chan, The Journal of Nutrition, Vol. 128, No. 10, October 1998, pp. 1593-1596.

In further embodiments, a polymer-containing portion of a stent delivery assembly can include a substance that reduces or prevents chemical degradation in the polymeric portion arising from exposure to radiation during sterilization. Various polymer-containing portions of a stent-delivery assembly can include such a substance, including, but not limited to a catheter, balloon, or restraining sheath. In some embodiments, the substance can be mixed or dispersed within the polymer-containing portion, such as within the body of the catheter, balloon, or restraining sheath.

Polymer containing portions can be fabricated using extrusion, injection molding, compression molding, rotational molding, dip coating, electrospinning, etc among the many processing possibilities. The substance can be incorporated into a polymer by solution blending, melt blending, imbibing, or a combination thereof. The polymer with the substance can then be processed by extrusion, injection molding, or other process to form a catheter, balloon, or sheath. Alternatively, the substance can be mixed with the polymer during extrusion or injection molding or the selected processing technique.

An embodiment of the invention is a stent delivery assembly comprising a polymeric portion of the assembly, the polymeric portion including a chemical degradation-reducing substance that reduces or prevents chemical degradation in the polymeric portion arising from exposure to radiation during sterilization; wherein the polymeric portion comprises a coating above a catheter, stent delivery balloon, or restraining sheath disposed over a stent disposed over the catheter, the coating including the substance dispersed within the coating.

Various free radical scavengers and antioxidants, both synthetic or natural, may be used to reduce or prevent chemical degradation in polymer-containing portions of a stent or stent delivery assembly. Representative examples of free radical scavengers or antioxidants that can be to reduce or eliminate chemical degradation due to radiation include, L-ascorbate (Vitamin C), Vitamin E, herbal rosemary, sage extracts, glutathione, melatonin, carotenes, resveratrol, butylated hydroxyanisole, butylated hydroxytoluene, propyl gallate, tertbutylhydroquinone, and combinations thereof. Various isomers of Vitamin E may be used, including the four tocopherols and four tocotrienols. The alpha, beta, gamma and delta forms of both the tocopherols and tocotrienols may be used to prevent chemical degradation. In particular, butylated hydroxytoluene can be used in drug-polymer layers to reduce or prevent degradation of active agents.

Low molecular weight free radical scavengers or antioxidants may be susceptible to leaching from polymer materials. Thus, such free radical scavengers or antioxidants may at least partially leach out of a polymer-containing portion of a stent or delivery assembly prior to radiation sterilization. Oligomeric or polymeric free radical scavengers or antioxidants are less susceptible to leaching from a polymer material. Thus, some embodiments can include using oligomeric or polymeric free radical scavengers or antioxidants in polymer-containing portions of a stent or delivery assembly. Representative examples of oligomeric or polymeric free radical scavengers or antioxidants include, but are not limited to, oligomeric or polymeric proanthocyanidins, polyphenols, polyphosphates, polyazomethine, high sulfate agar oligomers, chitooligosaccharides obtained by partial chitosan hydrolysis, polyfunctional oligomeric thioethers with sterically hindered phenols. Some polymeric free radical scavengers can be bonded or grafted on the backbone of a polymer to be protected and blended with additional polymer. The blend can then be used to fabricate a stent, coating, or part of a stent delivery system.

In further embodiments, a stent and stent delivery system that includes a free radical scavenger or antioxidant can be radiation sterilized in a vacuum or near vacuum environment. Ambient oxygen and oxygen dissolved in a polymer-containing portion of a stent or delivery assembly can facilitate chemical degradation induced by radiation. Thus, reducing or eliminating ambient and dissolved oxygen can further reduce such chemical degradation. In such embodiments, a pouch containing the stent and delivery assembly can be evacuated of air or other gas and sealed. A pouch can be evacuated using vacuum packaging or sealing equipment that are known to those of skill in the art of vacuum packaging.

In further embodiments, a stent and stent delivery system that includes a free radical scavenger or antioxidant can be radiation sterilized in an oxygen-free environment or gas. An oxygen free environment can include gases such as argon, nitrogen, or helium. After evacuating a pouch containing a stent and delivery system, the pouch can be filled with an oxygen free gas. "Oxygen-free" gas can refer to a gas that that includes no or substantially no oxygen. "Substantially no oxygen" can refer to a gas having less than 1%, 0.05%, or less than 0.01% oxygen.

Therefore, the modification of polymer properties due to radiation is generally due the reactions which are chemical in nature as well as the increase in temperature of a sample. Thus, it is believed that reducing the temperature of a polymer-containing device before, during, and after sterilization can slow down the rate of that the modification occurs which can reduce or eliminate adverse affects of radiation sterilization.

Furthermore, it is believed that the rate of at least some of the chemical degradation reactions induced by radiation decrease with temperature. In additional embodiments, a stent and delivery system can be radiation sterilized at a sterilization temperature (Ts) which is below an ambient temperature. Ambient temperature can refer to a temperature between about 15-30° C. In such embodiments, a stent and delivery system can be cooled to a Ts and then radiation sterilized. The Ts can be, for example, less than ambient temperature of the polymer. In various embodiments, Ts can be less than 10° C., 0° C., −15° C., −25° C., −40° C., −70° C., −100° C., −150° C., −200° C., −240° C., or less than −270° C. The stent and delivery system can be cooled to a Ts by various methods, such as, for example, by disposing the stent and delivery system in a freezer for a duration sufficient to cool the stent and delivery system to Ts. In additional embodiments, post-sterilization processing can be performed using a temperature cycle to quench or eliminate trapped radicals that were formed during the radiation sterilization process.

The underlying structure or substrate of a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

A polymer for use in fabricating an implantable medical device, such as a stent, can be biostable, bioabsorbable, biodegradable, biosoluble or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed and/or eliminated by the body. The processes of breaking down and absorption of the polymer can be caused by, for example, hydrolysis and metabolic processes. Biosoluble polymers clear the body by dissolution followed by elimination.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Representative examples of polymers that may be used to fabricate a substrate of an implantable medical device or a coating for an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), poly-orthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in fabricating an implantable medical device disclosed herein include ethylene vinyl alcohol copolymer (commonly known by the generic name EVOH or by the trade name EVAL™), poly(butyl methacrylate), poly(vinylidene fluoride-co-hexafluororpropene) (e.g., SOLEF® 21508, available from Solvay Solexis PVDF, Thorofare, N.J.), polyvinylidene fluoride (otherwise known as KYNAR®, available from Atofina Chemicals, Philadelphia, Pa.), ethylene-vinyl acetate copolymers, and polyethylene glycol.

A non-polymer substrate of an implantable medical device, such as a stent, may be made of a metallic material or an alloy such as, but not limited to, cobalt chromium alloy (ELGILOY®), stainless steel (316L), high nitrogen stainless steel, e.g., BIODUR® 108, cobalt chrome alloy L-605, "MP35N," "MP20N," ELASTINITE® (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Additionally, a coating for an implantable medical device can be composed of a non-polymer material. Non-polymer coatings include, but are not limited to, microporous carbon, metal, and ceramic.

A drug or active agent can include, but is not limited to, any substance capable of exerting a therapeutic, prophylactic, or diagnostic effect. The drugs for use in the implantable medical device, such as a stent or non-load bearing scaffolding structure may be of any or a combination of a therapeutic, prophylactic, or diagnostic agent. Examples of active agents include antiproliferative substances such as actinomycin D, or derivatives and analogs thereof. (manufactured by Sigma-Aldrich 1001 West Saint Paul Avenue, Milwaukee, Wis. 53233; or COSMEGEN™ available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (known by the name of everolimus), 40-O-(3-hydroxy)propyl-rapamycin, 40-O-[2-(2-hydroxy)ethoxy]ethyl-rapamycin, methyl rapamycin, and 40-O-tetrazole-rapamycin.

While particular embodiments of the present invention have been shown and described, it will be obvious to those skilled in the art that changes and modifications can be made without departing from this invention in its broader aspects.

What is claimed is:

1. A stent comprising:
   a polymeric portion;
   optionally, a drug; and
   a chemical degradation-reducing substance that reduces or prevents chemical degradation of a polymer of the polymeric portion, the optional drug, or both, the chemical degradation arising from exposure to radiation during sterilization;
   wherein the substance comprises a chitooligosaccharide obtained by partial chitosan hydrolysis.

2. The stent of claim 1, wherein the radiation comprises e-beam or gamma radiation.

3. The stent of claim 1, the polymeric portion comprises a biostable or bioabsorbable polymer, the substance being dispersed within the polymeric portion.

4. The stent of claim 1, wherein substance further comprises a free radical scavenger or antioxidant selected from the group consisting of L-ascorbate, Vitamin E, herbal rosemary, sage extracts, butylated hydroxyanisole, butylated hydroxytoluene, propyl gallate, tertbutylhydroquinone, and combinations thereof.

5. The stent of claim 1, wherein the polymeric portion is at least a part of a material from which the stent is formed.

6. The stent of claim 5, wherein the substance is dispersed within the polymeric portion.

7. The stent of claim 6, wherein the stent comprises a coating.

8. The stent of claim 7, wherein the coating comprises a drug.

* * * * *